United States Patent
Narvekar et al.

(10) Patent No.: US 10,207,832 B2
(45) Date of Patent: Feb. 19, 2019

(54) SUPPORTING STRUCTURE FOR SUPPORTING SEALED CARTRIDGES, TRANSPORT OR PACKAGING CONTAINER AND PROCESS FOR PROCESSING THE SAME

(71) Applicant: SCHOTT KAISHA PVT., LTD., Maharashtra (IN)

(72) Inventors: Anil Narayan Narvekar, Goa (IN); Pratul Prakash Potdar, Nani Daman (IN); Rishad Kairus Dadachanji, Mumabai (IN)

(73) Assignee: SCHOTT KAISHA PVT., LTD., Maharashtra (IN)

( * ) Notice: Subject to any disclaimer, the term of this patent is extended or adjusted under 35 U.S.C. 154(b) by 0 days.

(21) Appl. No.: 15/564,245

(22) PCT Filed: Oct. 16, 2015

(86) PCT No.: PCT/IN2015/000394
§ 371 (c)(1),
(2) Date: Oct. 4, 2017

(87) PCT Pub. No.: WO2016/166765
PCT Pub. Date: Oct. 20, 2016

(65) Prior Publication Data
US 2018/0126066 A1    May 10, 2018

(30) Foreign Application Priority Data
Apr. 17, 2015 (IN) .......................... 1590/MUM/2015

(51) Int. Cl.
*B65D 1/34* (2006.01)
*B65B 7/16* (2006.01)
(Continued)

(52) U.S. Cl.
CPC ............... *B65B 7/161* (2013.01); *A61J 1/062* (2013.01); *A61J 1/1412* (2013.01); *A61M 5/008* (2013.01);
(Continued)

(58) Field of Classification Search
CPC .. B65D 1/34; B65B 7/161; A61J 1/062; A61J 1/1412; B01L 3/5082
(Continued)

(56) References Cited

U.S. PATENT DOCUMENTS

| | | |
|---|---|---|
| 3,643,812 A | 2/1972 | Mander et al. |
| 8,118,167 B2 | 2/2012 | Togashi et al. |

(Continued)

FOREIGN PATENT DOCUMENTS

| | | |
|---|---|---|
| EP | 2183166 | 10/2014 |
| WO | 2015023924 | 2/2015 |

OTHER PUBLICATIONS

PCT/IN2015/000394; PCT International Search Report and Written Opinion of the International Searching Authority dated Apr. 13, 2016.
(Continued)

*Primary Examiner* — King M Chu
(74) *Attorney, Agent, or Firm* — Renner, Otto, Boisselle & Sklar, LLP

(57) ABSTRACT

A supporting structure for supporting a plurality of sealed medical cartridges is disclosed, comprising a planar supporting plate having a plurality of receptacles for accommodating the sealed cartridges. Retaining protrusions are formed at the bottom ends of the receptacles protruding inward, which are mated with the shoulder portions of the sealed cartridges in such a manner that the shoulder portions of the sealed cartridges are supported on the retaining protrusions of the receptacles and that the upper ends of the
(Continued)

sealed cartridges protrude from the upper ends of the receptacles at an upper side of the planar supporting plate, when the sealed cartridges are accommodated upside-down in the receptacles. The inventive nest will be suitable for any nested liquid filling machine without much changes in filling table and general settings.

19 Claims, 11 Drawing Sheets

(51) Int. Cl.
| | |
|---|---|
| *A61M 5/00* | (2006.01) |
| *B65B 31/02* | (2006.01) |
| *B65B 3/00* | (2006.01) |
| *B01L 3/00* | (2006.01) |
| *B01L 9/06* | (2006.01) |
| *A61J 1/06* | (2006.01) |
| *A61J 1/14* | (2006.01) |
| *B65B 7/28* | (2006.01) |
| *B65B 43/59* | (2006.01) |
| *B65B 43/54* | (2006.01) |
| *B65B 55/04* | (2006.01) |
| *B65B 55/20* | (2006.01) |
| *B65B 61/20* | (2006.01) |
| *B65B 39/00* | (2006.01) |

(52) U.S. Cl.
CPC ............ *B01L 3/5082* (2013.01); *B01L 3/523* (2013.01); *B01L 9/06* (2013.01); *B65B 3/003* (2013.01); *B65B 7/2821* (2013.01); *B65B 31/027* (2013.01); *B65B 39/00* (2013.01); *B65B 43/54* (2013.01); *B65B 43/59* (2013.01); *B65B 55/04* (2013.01); *B65B 55/20* (2013.01); *B65B 61/207* (2013.01); *B01L 2200/185* (2013.01); *B01L 2300/042* (2013.01); *B01L 2300/044* (2013.01); *B01L 2300/0835* (2013.01); *B01L 2300/123* (2013.01); *B65B 2039/009* (2013.01)

(58) Field of Classification Search
USPC ........................................................ 206/557
See application file for complete search history.

(56) References Cited

U.S. PATENT DOCUMENTS

| | | | |
|---|---|---|---|
| 8,561,828 | B2 | 10/2013 | Krauss et al. |
| 2005/0013745 | A1* | 1/2005 | Buchanan ............ B01L 3/50855 422/400 |
| 2005/0214924 | A1 | 9/2005 | Glaser et al. |
| 2009/0095647 | A1 | 4/2009 | Togashi et al. |
| 2009/0238727 | A1* | 9/2009 | Sinclair ................... B01L 9/06 422/400 |
| 2010/0012546 | A1* | 1/2010 | Togashi ................ A61M 5/008 206/534.1 |
| 2011/0192756 | A1 | 8/2011 | Hill |
| 2011/0226662 | A1 | 9/2011 | Nicoletti |
| 2012/0248057 | A1 | 10/2012 | Bogle et al. |
| 2013/0048531 | A1 | 2/2013 | Nicoletti |
| 2013/0161225 | A1 | 6/2013 | Lepot |
| 2014/0027332 | A1 | 1/2014 | Pawlowski et al. |
| 2015/0089830 | A1 | 4/2015 | Wissner et al. |
| 2015/0272827 | A1 | 10/2015 | Tsukiji |

OTHER PUBLICATIONS

PCT/IN2015/000394; PCT International Preliminary Report on Patentability dated Jul. 19, 2017.

* cited by examiner

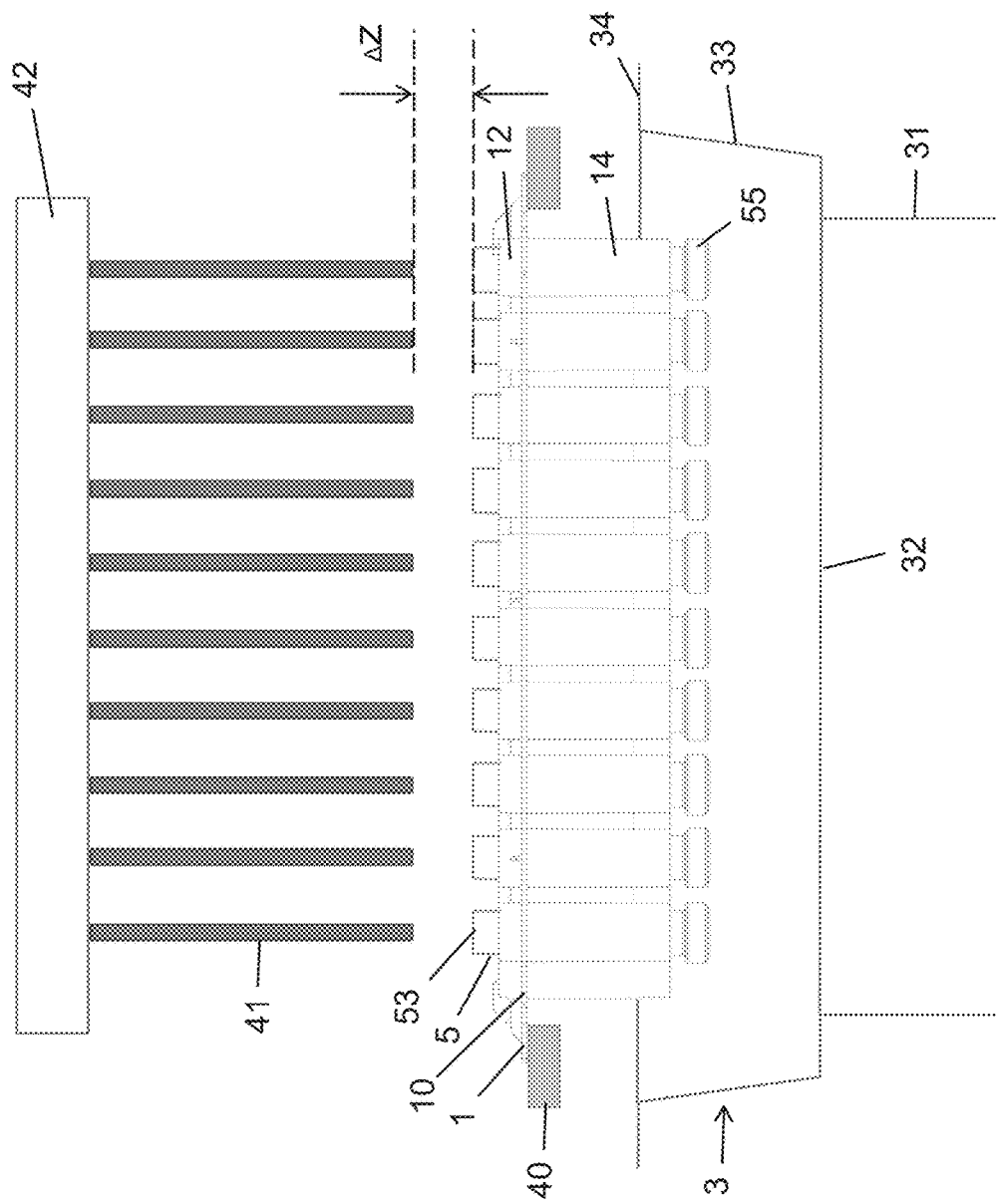

SUPPORTING STRUCTURE FOR SUPPORTING SEALED CARTRIDGES, TRANSPORT OR PACKAGING CONTAINER AND PROCESS FOR PROCESSING THE SAME

The present application is a U.S. National Stage Application based on and claiming benefit and priority under 35 U.S.C. § 371 of International Application No. PCT/IN2015/000394, filed 16 Oct. 2015, which in turn claims benefit of and priority to Indian Application No. 1590/MUM/2015 filed 17 Apr. 2015, the entirety of both of which is hereby incorporated herein by reference.

FIELD OF INVENTION

The present invention relates in general to the processing of a batch of sealed cartridges, particularly of pre-crimped cartridges, for use in pharmaceutical, medical or cosmetic applications and relates in particular to a supporting structure (also named nest) provided for holding sealed or pre-crimped cartridges for filling and stoppering operation. Further aspects of the present invention relate to a nest and tub assembly accommodating sealed cartridges, which can be directly fed on existing filling and stoppering machine set-ups for processing sealed prefillable syringe barrels.

BACKGROUND OF INVENTION

Conventionally presterilized prefillable syringe barrels are supplied in tub and nest assemblies that are hermetically sealed to the environment to pharmaceutical customers, who then fill medicine into the presterilized nested syringe barrels under sterile conditions using filling and stoppering machines. In the market there are three types of filling and stoppering machines available, namely 1) manual machines, 2) semi automatic machines and 3) fully automatic machines.

There is one tub and nest format available in the market for pre-crimped cartridges but there are lots of disadvantages to use this existing tube and nest format with existing as well as new filling and stoppering machines because this tub and nest format requires complete setting change from infeed to outfeed for accommodating different height level of cartridge into the nest. Moreover a complete replacement of filling carriers is required for maintaining the height between the filling nozzles and the cartridge top level. Further the drawback of two different change parts needs separate validation study as per GMP (Good Manufacturing Practice) guidelines requirements. If one tries to fill the pre-crimped cartridge nest available in the market on the same machine without changing the machine height setting accidents will happen which may cause damage to the filling nozzles or glass cartridges may get broken because the height difference between the filling nozzles and the pre-crimped cartridges is too small.

These disadvantages similarly hold 1) for manual filling and stoppering machines, which are operated electrically and pneumatically and where the processes are triggered by an operator, 2) for semi automatic filling and stoppering machines, which are operated electrically, electronically and pneumatically and where the operator has to remove the outer bag of the tub and nest assembly and then a top lid from the tub along with an inner sheet, and 3) for fully automatic filling and stoppering machines, which are operated electrically, electronically and pneumatically and where whole packets are inserted into the filling and stoppering machine one by one, the machine will automatically remove the outer bag and then remove the top lid from the tub by means of an automatic peeling off unit, then the inner sheet of the tub and nest assembly will be removed automatically and the machine will then automatically pick up the nests by means of a vacuum cup and place them onto transport carriers, which are then moved towards the filling station nozzles for the medicine filling process.

The currently available tub and nest assemblies in the market require the replacement of filling carriers for maintaining an accurate height difference between the filling nozzles and the cartridge top levels. Further after replacement of the filling carriers the replacement parts require separate validation studies as per GMP guidelines requirements. If the tub and nest assemblies available in the market are directly fed for filling of pre-crimped cartridges on the same machine without any alterations in the filling machines then the filling nozzles can be damaged or glass cartridges can be broken because the height difference between the filling nozzles and the pre-crimped cartridges is too small. All the above activities will incur higher costs and also additional time will be required to change the parts resulting in production losses. Further all fully automatic machines and new separate change parts are very expensive.

U.S. Pat. No. 8,561,828 B2 discloses a nest for concurrently holding a plurality of cylindrical pharmaceutical containers, such as vials or cylindrical ampoules, that have no retaining edges like the hand rests of conventional syringe bodies. The nest comprises a plurality of cylindrical receptacles for accommodating the cylindrical containers. At the bottom ends of the receptacles two opposite retaining protrusions are provided, for limiting an axial movement of the cylindrical containers and directly supporting the bottoms of the cylindrical containers. Each receptacle has two opposite apertures so that a lifting element of a manipulating device can directly engage with the bottoms of the containers to properly adjust their height levels. The containers are, however, accommodated upright in the receptacles.

US 2013/0048531 A1 discloses a similar nest, wherein each of the receptacles is formed by a plurality of side-walls that are spaced apart from each other but not unitary, circumferential side-walls. At the bottom ends of the side-walls retaining protrusions are provided. Also this nest can only be used for cylindrical pharmaceutical containers, such as vials or cylindrical ampoules, that have no retaining edges like the hand rests of conventional syringe bodies.

EP 2 183 166 B1 of the same applicant discloses a similar nest where the pharmaceutical containers are either accommodated in tubular receptacles having a closed bottom or hang with their neck portions in openings provided in the supporting plate of the nest.

U.S. Pat. No. 8,118,167 B2 discloses a transport container for sealed prefillable syringe barrels. The transport container accommodates a nest having cylindrical receptacles provided on the upper side thereof. The syringe barrels hang with their hand rests on the upper rims of the cylindrical receptacles. The bottom ends of the syringe barrels are sealed and extend into the free inner volume of the transport container. The bottom ends of the syringe barrels are not supported by holding members.

US 2013/0161225 discloses a further packaging unit for storing syringe barrels, wherein the syringe barrels again hang with their hand rests on the upper rims of the cylindrical receptacles. An upper lid can be clipped onto the nest to secure the syringe barrels and provide an integral cover. A similar tube storage rack is disclosed by U.S. Pat. No. 3,643,812.

US 2005/0214924 A1 discloses a supporting structure for sampling tubes containing culture growth media. The supporting structure comprises a supporting plate having a plurality of cup-shaped receptacles with bottoms on which the bottoms of the sampling tubes are directly supported. Here, the sampling tubes are supported in an upright position and with their upper ends protruding beyond the supporting plate so that the filling openings are easily accessible.

SUMMARY OF INVENTION

It is an object of the present invention to provide an enhanced supporting structure for supporting a plurality of sealed cartridges that can overcome the above drawbacks, particularly that can ensure a proper height difference between members of a processing station, such as filling nozzles, and the sealed cartridges to be processed to thereby enable an efficient processing of the cartridges. Further, a transport or packaging container accommodating such a supporting structure is to be provided. It is a further object of the present invention to provide This problem is solved by a supporting structure for supporting a plurality of sealed cartridges for use in pharmaceutical, medical or cosmetic applications as claimed in claim 1, by a transport or packaging container accommodating such a supporting structure as claimed in claim 8 and by a process for processing a batch of sealed cartridges using such a supporting structure as claimed in claim 10. Further advantageous embodiments are the subject-matter of the dependent claims.

According to the present invention there is provided a supporting structure for supporting a plurality of sealed cartridges for use in pharmaceutical, medical or cosmetic applications, said cartridges having an upper end and a bottom end opposite to the upper end, a cylindrical body of a first outer diameter with a filling opening at the upper end, and a shoulder portion at the bottom end with a secondary opening which is sealed by a seal, a predetermined axial length being defined between the upper end and the bottom end. The supporting structure comprises a planar supporting plate, and a plurality of tubular receptacles formed at the planar supporting plate in a regular arrangement and extending downward from a bottom side of the planar supporting plate for accommodating the sealed cartridges, wherein retaining protrusions are formed at the bottom ends of the receptacles protruding inward, and the axial length of the receptacles is smaller than the axial length of the sealed cartridges.

According to the present invention the retaining protrusions are mated with the shoulder portions of the sealed cartridges in such a manner that the shoulder portions of the sealed cartridges are supported on the retaining protrusions of the receptacles and that the upper ends of the sealed cartridges protrude from the upper ends of the receptacles at an upper side of the planar supporting plate, when the sealed cartridges are accommodated upside-down in the receptacles.

Because the seals of the cartridges at their bottom ends, which are susceptible to damage upon application of excessive forces, do not rest on a supporting surface the cartridges, once filled, may be stoppered (closed at their upper ends with rubber plugs, plungers or similar sealing members) without damaging the seals at the bottom ends. At the same time, the filling openings, which extend beyond the upper rims of the receptacles, are freely accessible for processing.

According to a further embodiment the receptacles are of cylindrical shape and a plurality of ribs are formed at equidistant angular spacing on inner circumferential side-walls of the receptacles, preferably at diametrally opposite positions thereof, wherein the ribs protrude radially inward from the inner circumferential side-walls of the receptacles for centering the sealed cartridges inside the receptacles. Thus, a reliable centering of the cartridges, a rattle-free storage inside the receptacles and a smooth, rattle-free insertion into and removal out of the receptacles may be accomplished. Further, forces exerted e.g. upon stoppering may be distributed more efficiently without deformation of the receptacles, thus ensuring a more precise centering and positioning of the cartridges inside the receptacles.

According to a further embodiment the retaining protrusions are formed as ring segments that protrude radially inward at the bottom ends of the receptacles and at equidistant angular spacing, preferably at diametrally opposite positions thereof, thus enabling a more uniform distribution of forces, particularly upon stoppering.

According to a further embodiment an outer diameter of the sealed cartridges at their shoulder portions is larger than the outer diameter at their sealed bottom ends but smaller than the first outer diameter. Further the thickness of the retaining protrusions in the axial direction may be smaller than the axial length of the sealed bottom ends so that the sealed bottom ends of the sealed cartridges extend through openings formed by the retaining protrusions at the bottom ends of the receptacles. The sealed bottom ends of the cartridges thus do not rest on any supporting surfaces but hang free in space, thereby reducing the risk of mechanical damage upon stoppering and related processing steps.

According to a further embodiment the supporting plate is formed of a plastic material and the side-walls of the receptacles and the retaining protrusions are formed unitary with the supporting plate, wherein the retaining protrusions are configured to sustain axial forces exerted onto the sealed cartridges of up to 1,000 N, preferably of up to 750 N and more preferably of up to 500 N.

According to a further embodiment the front ends of the retaining protrusions are wedge-shaped in correspondence with the outer contour of the shoulder portions of the sealed cartridges, thus enabling a more reliable and precise supporting of the shoulder portions and even less deformation of the retaining protrusions upon stoppering or related processing steps.

According to a further embodiment virtual connecting lines between the centers of directly adjacent receptacles respectively form a hexagon with a further receptacle disposed at a center of the respective hexagon, wherein the receptacles extend beyond the upper surface of the supporting plate and stiffening ribs protruding upward from the upper surface of the supporting plate are formed on the upper surface of the supporting plate so as to connect the circumferential side walls of the receptacles, for stiffening the supporting plate. Thus, a rather efficient stiffening of the supporting plate may be accomplished.

According to a further aspect of the present invention there is provided a transport or packaging container (tub) for accommodating a plurality of sealed cartridges for use in pharmaceutical, medical or cosmetic applications, wherein the transport or packaging container is box-shaped and comprises a bottom, which is closed or sealed by a seal, upstanding lower side-walls extending essentially perpendicularly from said bottom, a circumferential supporting step extending horizontally from said side-walls, upper side-walls extending upward from said supporting step and a circumferential flange formed at upper ends of the side-walls. A supporting structure (nest) as disclosed hereinafter in more detail is accommodated in the transport or packaging container and supports a plurality of sealed cartridges in the receptacles thereof. The nest rests directly on the supporting step of the tub. Thus, regardless of whether the cartridges are processed while being accommodated only in the nest or in a tub and nest assembly it can be ensured that the upper ends of all cartridges are on the same height level. Thus, a precise distance between the upper ends of the cartridges and the bottom ends of filling nozzles or the like can be ensured reliably, thus avoiding breakage or damage during processing of the cartridges.

According to a further embodiment the transport or packaging container further comprises a flexible lid sealed onto the circumferential flange of the transport or packaging container for sealing the transport or packaging container, preferably for hermetically sealing the inner volume of the transport or packaging container against the environment.

According to a further aspect of the present invention there is provided a process for processing a batch of sealed cartridges for use in pharmaceutical, medical or cosmetic applications, comprising the steps of: a) providing a supporting structure as disclosed hereinafter in more detail; b) disposing the sealed cartridges upside-down in the receptacles and with their upper ends protruding from the upper ends of the receptacles at an upper side of the planar supporting plate so that the shoulder portions of the sealed cartridges are supported on the retaining protrusions of the receptacles and the upper ends of the sealed cartridges are disposed at the same height level; c) feeding the supporting structure with the sealed cartridges to a processing station; and d) processing the sealed cartridges at their upper ends at the processing station while being supported by the supporting structure.

According to a further embodiment step d) comprises one or more of the following: filling the sealed cartridges via the filling openings at the upper ends; stoppering the sealed cartridges at their upper ends using rubber stoppers; pre gassing and post gassing.

According to a further embodiment the process further comprises: disposing the supporting structure in a frame-like holding table; feeding the supporting structure together with the sealed cartridges to the processing station while being supported by the frame-like holding table; and disposing the supporting structure with the sealed cartridges inside a box-shaped transport or packaging container after said step d), which comprises a bottom, upstanding lower side-walls extending essentially perpendicularly from said bottom, a circumferential supporting step extending horizontally from said side-walls, upper side-walls extending upward from said supporting step and a circumferential flange formed at upper ends of the side-walls so that the edge of the planar supporting plate of the supporting structure is supported on the circumferential supporting step of the transport or packaging container, the upper ends of the sealed cartridges do not protrude beyond the circumferential flange of the transport or packaging container, and the bottom ends of the sealed cartridges are disposed spaced apart from the bottom of the transport or packaging container.

According to a further embodiment the process further comprises: disposing the supporting structure with the sealed cartridges inside a box-shaped transport or packaging container, which comprises a bottom, upstanding lower side-walls extending essentially perpendicularly from said bottom, a circumferential supporting step extending horizontally from said side-walls, upper side-walls extending upward from said supporting step and a circumferential flange formed at upper ends of the side-walls so that the edge of the planar supporting plate of the supporting structure is supported on the circumferential supporting step, the upper ends of the sealed cartridges do not protrude beyond the circumferential flange of the transport or packaging container, and the bottom ends of the sealed cartridges are disposed spaced apart from the bottom of the transport or packaging container; wherein step c) further comprises: disposing the transport or packaging container in a frame-like holding table so that the supporting step of the transport or packaging container is supported on an upper side of the frame-like holding table and that the upper ends of the sealed cartridges are disposed at the same height level; and feeding the frame-like holding table together with the transport or packaging container, the supporting structure accommodated therein and the sealed cartridges to the processing station.

According to a further embodiment the transport or packaging container is sealed with a flexible lid.

According to a further embodiment of the process the sealed cartridges are pre-crimped cartridges.

OVERVIEW ON DRAWINGS

Hereinafter, the present invention will be disclosed in exemplary manner and with reference to the drawings, wherein:

FIG. 11 is a schematic cross-sectional view of the tub and nest assembly at a filling station used in a process according to the present invention.

Throughout the drawings, the same reference numerals designate identical or substantially the same components or groups of components.

DETAILED DESCRIPTION OF PREFERRED EMBODIMENTS

A supporting structure (in the following nest) in the sense of the present invention is used for concurrently supporting a plurality of sealed cartridges for use in pharmaceutical, medical or cosmetic applications. Such cartridges, including pen cartridges, by-pass cartridges and dental cartridges, are a commonly-used packaging solution for drug delivery systems, e.g. insulin administration, pen systems, pump systems, auto-injectors and needle free injectors. For special requirements such as by-pass and chemically strengthened cartridges, personalized designs are available on the market. Cartridges available on the market may be made of glass material, particularly of Fiolax® glass from SCHOTT AG, and offer fixed volumes for drug delivery of e.g. 1.0 ml, 1.5 ml and 3.0 ml. Different volumes usually correspond to different axial lengths of the cartridges.

Figure 6:
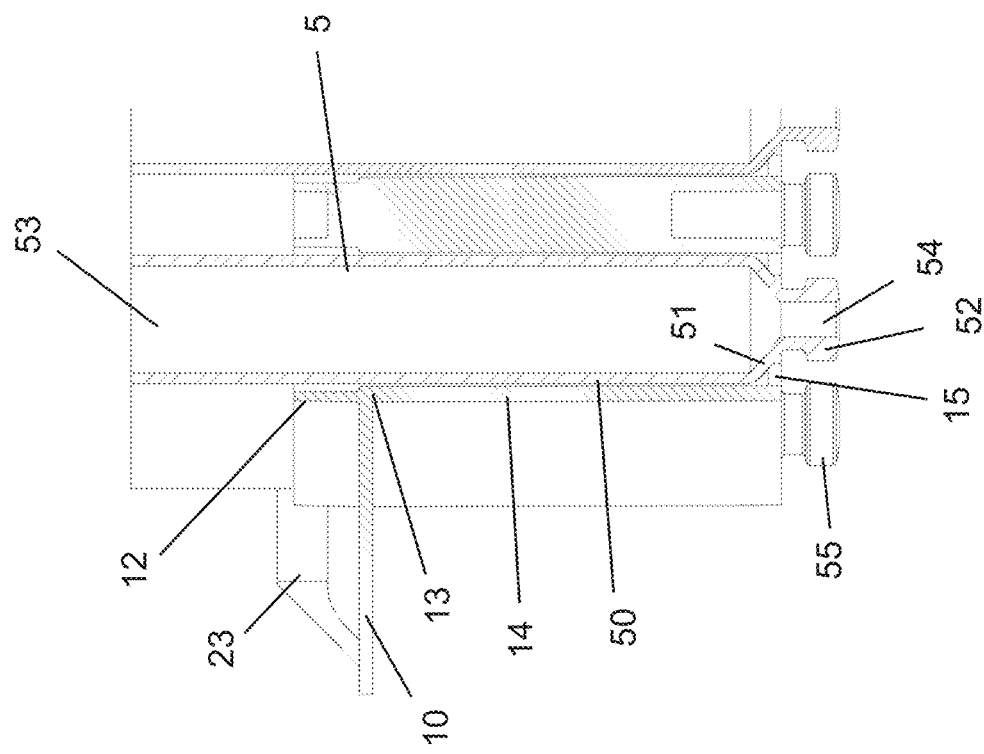
FIG. 6 is an enlarged partial view from FIG. 5 showing how the cartridges are supported inside the receptacles of the supporting structure according to the present invention.

An example for such a cartridge embodied as a syringe barrel is shown in FIG. 6 and comprises an upper end with a filling opening 53, a bottom end 52 opposite to the upper end and a cylindrical body 50 of a first outer diameter, which is usually identical with the diameter of the filling opening 53 at the upper end of the syringe barrel. The cylindrical body 50 merges into a tapered shoulder portion 51 at the bottom end of a reduced diameter, which is followed by widened bottom rim 52 with a secondary opening 54 used for drug administering. After filling the cylindrical body 50, the filling opening 53 is closed by means of an elastomeric closure provided with or without a fluoropolymer barrier coating, such as a thick rubber or plastic plug, which later acts as a piston when the content is pressed out for drug administering. The secondary opening 54 is sealed by a seal, usually with a rubber plug with septum (puncture rubber) provided with or without a fluoropolymer barrier coating or with a combiseal. For protecting the septum and fixing the plug an outer closure (beaded cap or cramp), often made from an aluminum sheet or aluminum/plastic compound material, is used, which is usually crimped over the widened bottom rim 52 to thereby tightly secure the seal at the cartridge and thereby form a pre-crimped cartridge in the sense of the present application. In the cross-sectional view of FIG. 6 such a pre-crimped cartridge including a seal 55 of the type mentioned above is shown on the right-hand and left-hand side of the drawing, whereas the central cartridge is shown in a cross-section and without such a seal. As can be concluded from FIG. 6, a predetermined axial length is defined between the upper end and the bottom end of the cartridge. Particularly, cartridges in the sense of the present invention do not have hand rests at their upper ends as conventional syringe bodies, and, if they would have such fingers rests, these hand rests would not be supported directly on a supporting plate or on members thereof, as outlined in more detail in the following, when such cartridges were accommodated in a nest.

Figure 1:
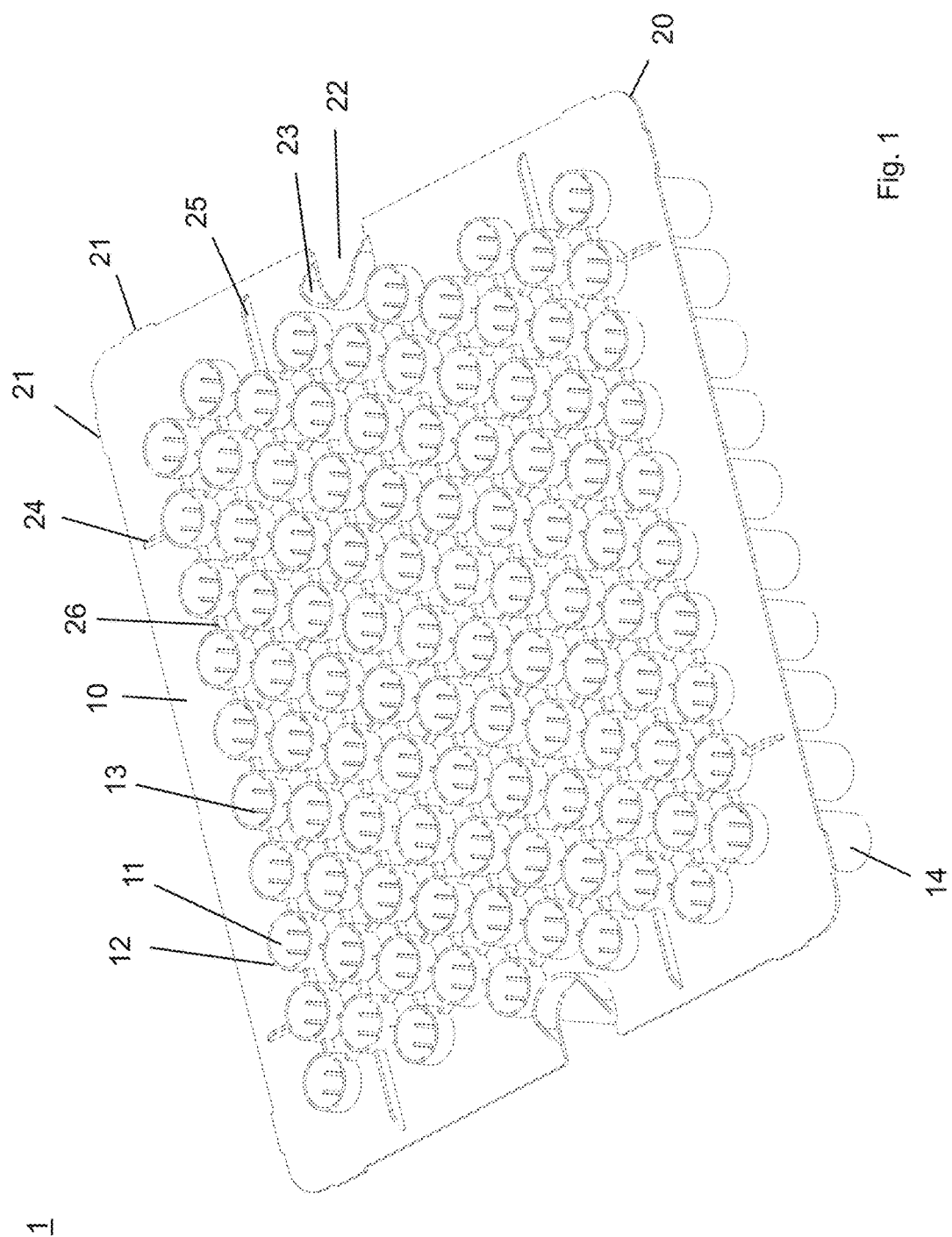
FIG. 1 is a perspective top view of a supporting structure according to the present invention.

Referring to FIGS. 1 to 4, a supporting structure (in the following nest) comprises a planar supporting plate 10 having a plurality of tubular receptacles 11 disposed in a regular arrangement, which at least extend downward from the bottom side of the planar supporting plate 11 (see bottom view of FIG. 4), and preferably also protrude upward from the upper side of the supporting plate, as shown in the perspective top view of FIG. 1. Thus, the tubular receptacles 11 are formed by the circumferential side-walls 12, 14 protruding from the upper and bottom side of the supporting plate 10, respectively. Preferably these side-walls 12, 14 are of cylindrical shape for accommodating the cartridges, although other shapes, such as polygonal shapes are also possible. These receptacles 11 are disposed in a regular two-dimensional arrangement, at equidistant spacing. As shown in the top view of FIG. 2, virtual connecting lines between the centers of directly adjacent receptacles 11 respectively may form a hexagon with a further receptacle 11 disposed at a center of the respective hexagon. According to other embodiments, the receptacles may also be disposed at equidistant spacing along two mutually orthogonal directions.

The inner diameter of the receptacles is slightly larger than the outer diameter of the cartridges to be accommodated. For enabling a precise centering of the cartridges, a plurality of ribs 13 is formed on the inner circumferential surfaces of the side-walls 12, 14 protruding radially inward. These ribs 13 are formed at equidistant angular spacing on the inner surfaces of the side-walls 12, 14, preferably at diametrally opposite positions thereof, so that the total number of these ribs 13 may be e.g. equal to four or eight.

The upper ends of these ribs 13 preferably do not extend up to the upper rim of the side-walls 12. In order to enable a smooth insertion of the cartridges into the receptacles 11, the upper ends of the ribs 13 are preferably slanted radially inward to guide the cartridges upon insertion. Together, the ribs 13 span an inner volume of a diameter, which essentially equals the outer diameter of the cartridges, thus enabling an essentially rattle-free storage of the cartridges and a smooth, rattle-free axial movement of the cartridges upon insertion into or removal out of the receptacles 11. The ribs 13 enable a precise centering of the cartridges at predetermined positions, so that automated processing systems may expect the cartridges at precisely predetermined positions upon their transfer to a processing station, which significantly reduces the efforts required for automation.

As shown in FIG. 6, the axial length of the receptacles 11 is smaller than the axial length of the cartridges to be accommodated, so that in use the upper ends with the filling openings 53 extend beyond the upper rim of the upper side-walls 12 of the receptacles so that the filling openings 53 are freely accessible for processing, e.g. for performing a filling operation as shown in FIG. 11.

Figure 4:
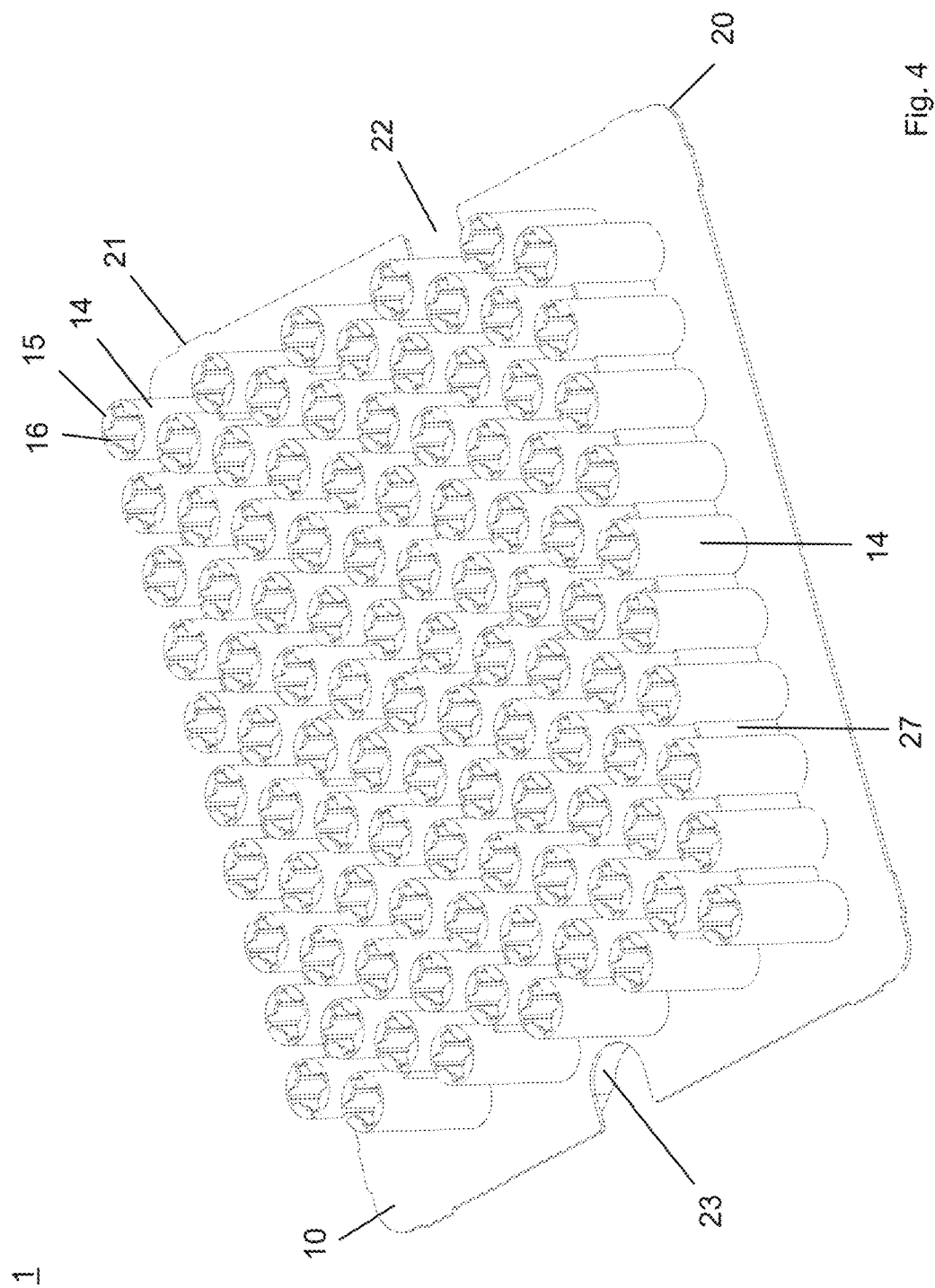
FIG. 4 is a perspective bottom view of the supporting structure of FIG. 1.
Figure 5:
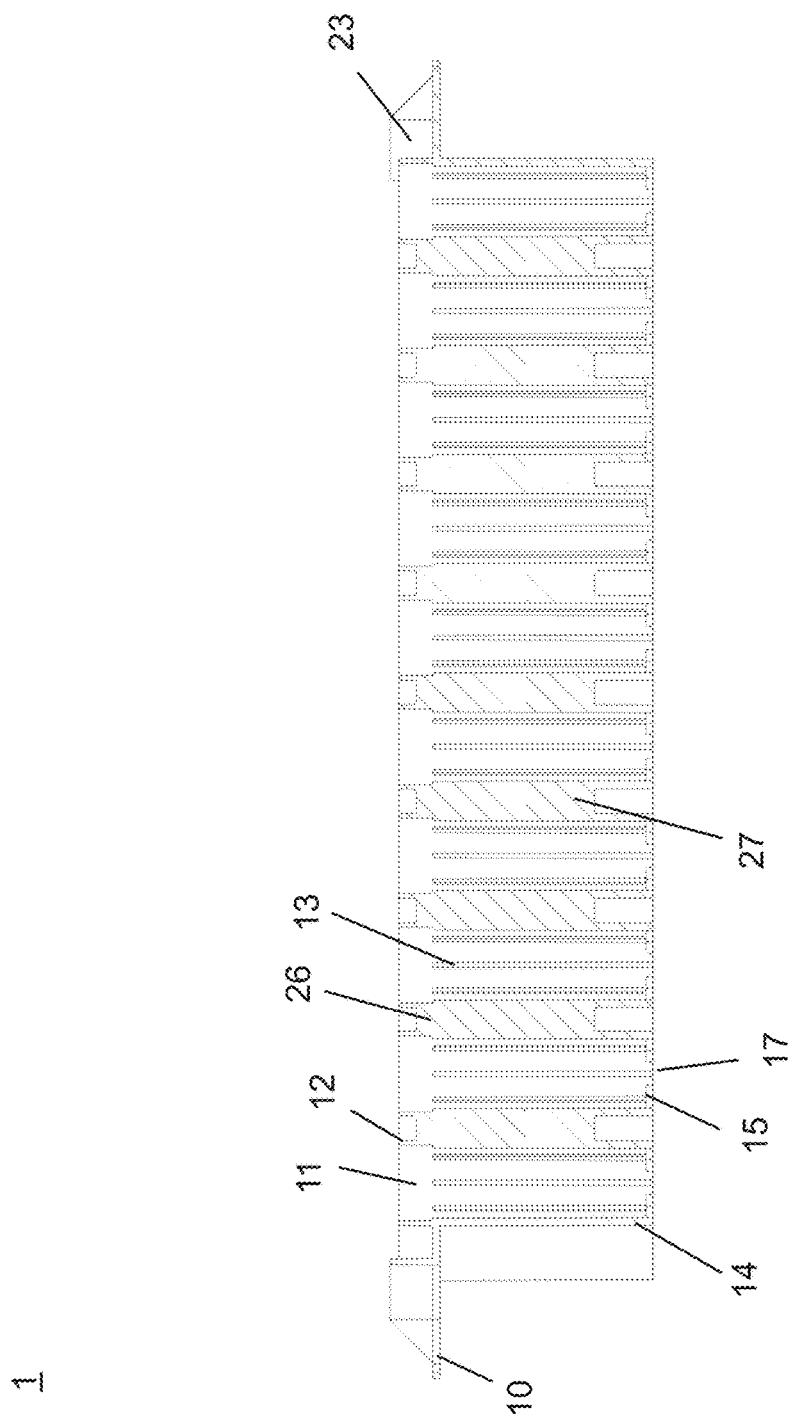
FIG. 5 is a schematic cross-section of the supporting structure of FIG. 1 without cartridges.

As shown in FIGS. 4 to 6, retaining protrusions 15 are formed at the bottom ends of the receptacles 11 protruding radially inward. These retaining protrusions 15 are mated with the shoulder portions 51 of the cartridges in such a manner that the shoulder portions 51 are directly supported on the retaining protrusions 15 of the receptacles 11 when the cartridges are accommodated upside-down in the receptacles 11, as shown in FIG. 6. Furthermore, the axial length of the receptacles is mated such to that of the cartridges that the upper ends of the cartridges protrude from the upper ends of the receptacles 11, as shown in FIG. 6.

Figure 3:
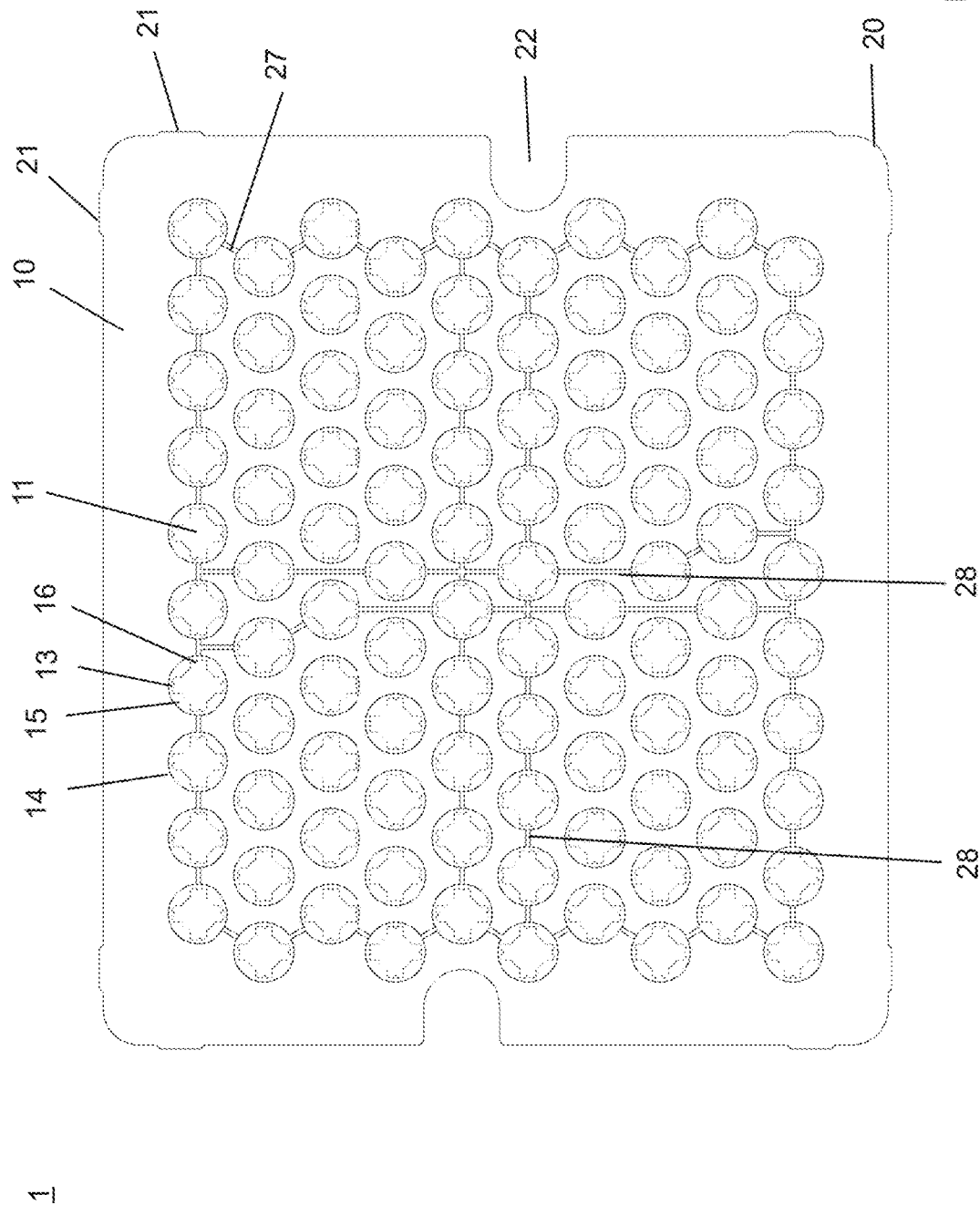
FIG. 3 is a bottom view of the supporting structure of FIG. 1.

As shown in FIGS. 3 and 4, the retaining protrusions 15 are formed as ring segments that protrude radially inward at the bottom ends of the receptacles 11 and at equidistant angular spacing, preferably at diametrally opposite positions. As shown in FIG. 3, gaps 16 of essentially rectangular profile are formed between adjacent ones of the retaining protrusions 15. These gaps 16 preferably extend up to the inner surface of the side-walls 14 of the receptacles 11. The afore-mentioned axial ribs 13 may extend downward to the retaining protrusions 15, but for a precise centering of the cartridges this is not essential.

For a smooth and more stable and precise supporting of the cartridges, the front ends of the retaining protrusions 15 may be slanted or wedge-shaped in correspondence with the outer contour of the shoulder portions 51 of the cartridges to be accommodated.

As shown in FIG. 6, the outer diameter of the sealed or pre-crimped cartridges 5 at their shoulder portions 51 is larger than the outer diameter at their sealed bottom ends 54 but smaller than the (first) outer diameter of the cylindrical body 50. Further, the thickness of the retaining protrusions 15 in axial direction is smaller than the axial length of the sealed bottom ends of the sealed cartridges 5 so that the sealed bottom ends of the sealed cartridges extend through central openings 17 (shown in FIG. 5) formed by the retaining protrusions 15 at the bottom ends of the receptacles 11.

The supporting plate 10 of a nest 1 according to the present invention is preferably formed of a plastic material and the side-walls 12, 14 of the receptacles 11 and the retaining protrusions 15 are thus formed unitary with the supporting plate 10. For enabling a stoppering of the filling openings 53 with rubber plugs or syringe plungers while the cartridges are accommodated in the receptacles 11 of the nest 1, the retaining protrusions 15 are preferably configured to sustain typical axial forces exerted onto the sealed cartridges upon stoppering of up to 500 N, preferably of up to 750 N and more preferably of up to 1,000 N, which can be ensured easily by a suitable choice of the plastic material and material strength of the supporting plate 10 and all its members.

Figure 2:
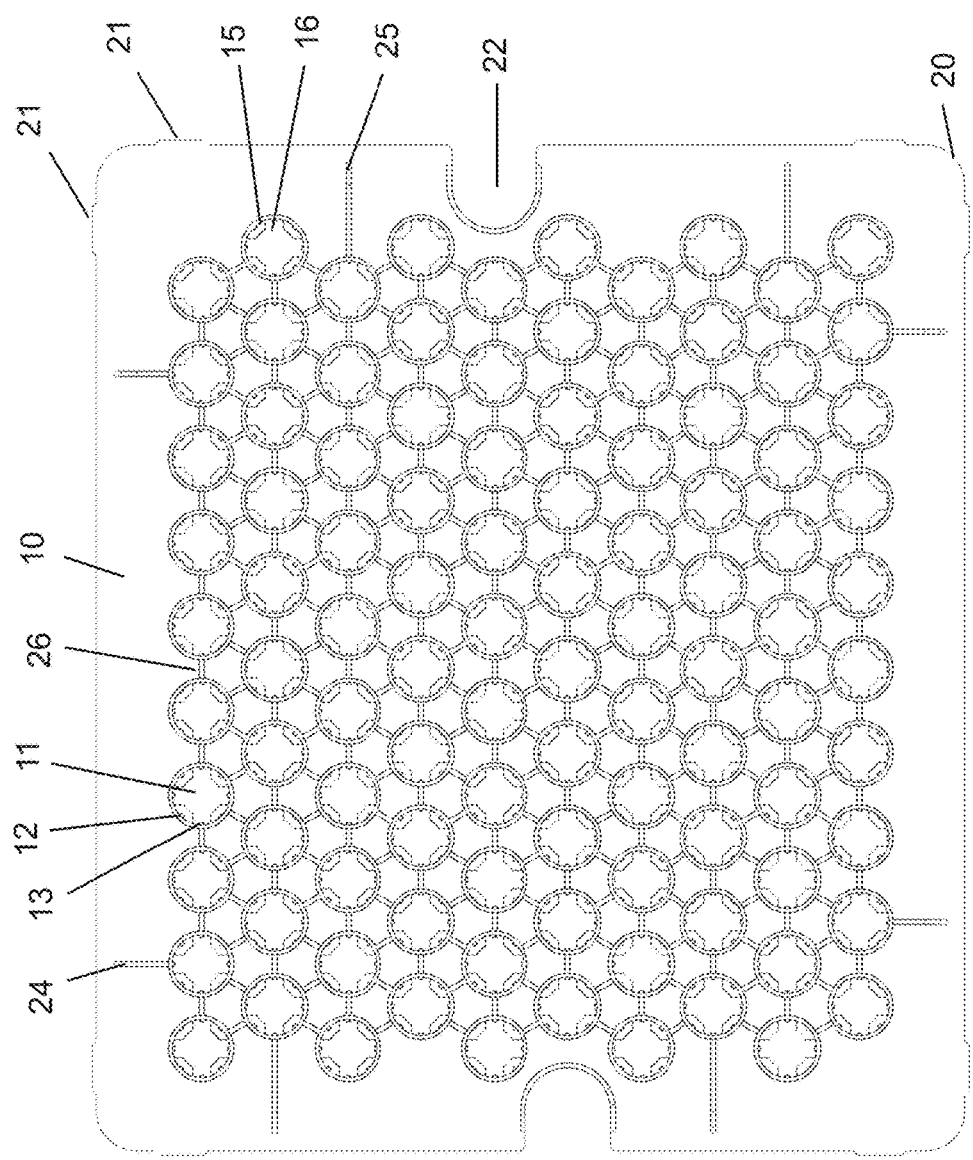
FIG. 2 is a top view of the supporting structure of FIG. 1.

As shown in FIGS. 2 and 4, for stiffening the supporting plate 10, stiffening ribs 26, 27, 28 may be provided on the upper side and bottom side, respectively, of the supporting plate 10, connecting the upper side-walls 12 and bottom side-walls 14 of the receptacles. In the arrangement of the receptacles 11 shown in FIG. 2, these stiffening ribs 26 thus form hexagons interconnecting directly adjacent ones of the receptacles and triangles connecting the outer ones of these receptacles with a further receptacle 11 disposed in the center of a respective hexagon. As shown in FIG. 4, these stiffening ribs 27 may interconnect the side-walls 14 of the outer ones of the receptacles 11. Furthermore, central stiffening ribs 28 may also be provided near the center of the supporting plate 10, for interconnecting central ones of these receptacles 11. In a preferred embodiment, such a nest 1 will be made of a plastic material using plastic injection-molding techniques. Despite the afore-mentioned stiffening measures, the supporting plate 10 may still be flexible to a certain extent, if required.

Figure 7:
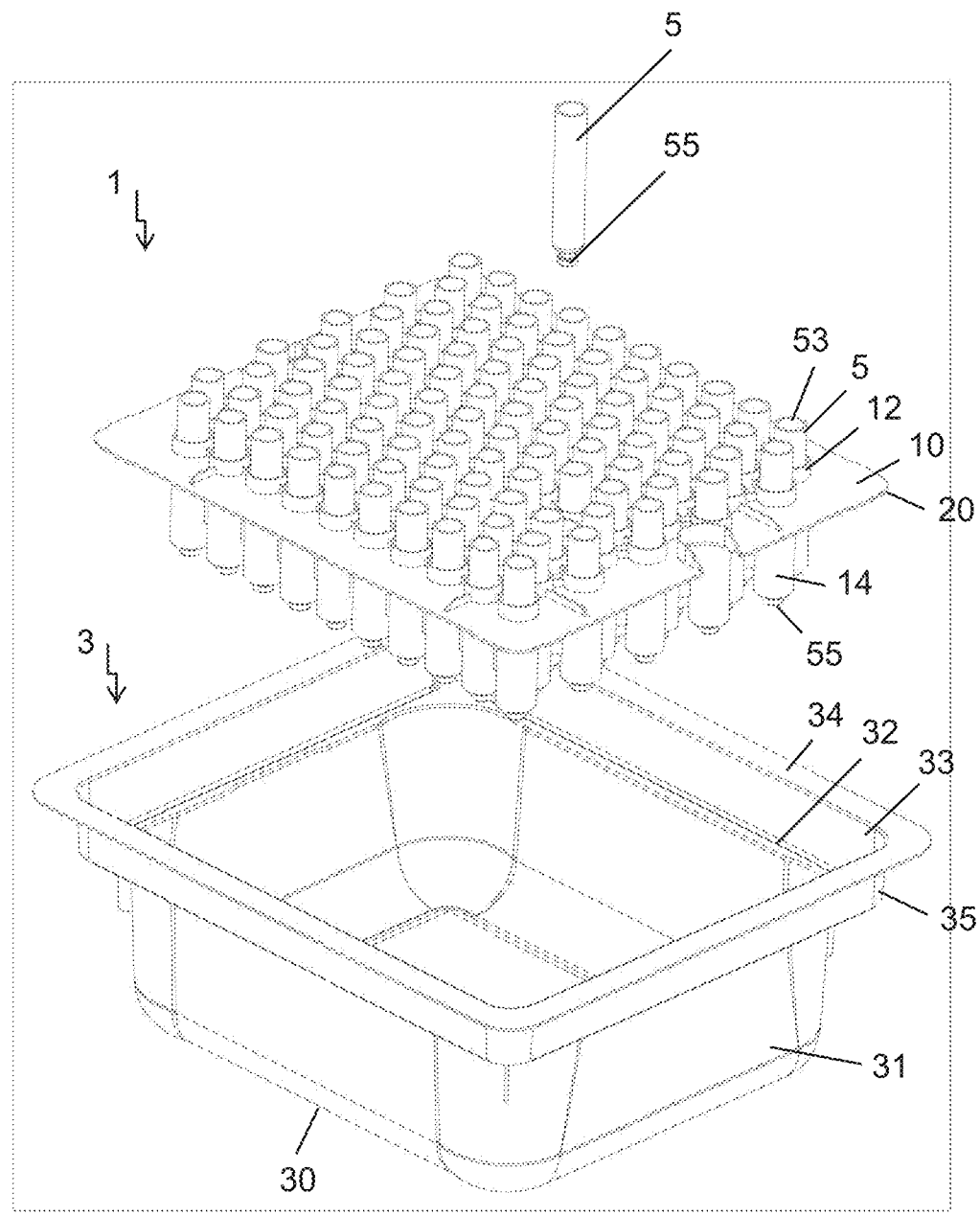
FIG. 7 is an exploded view showing a transport or packaging container together with the supporting structure of FIG. 1 (tub and nest assembly) with cartridges inserted into the receptacles of the supporting structure and with one cartridge sealed at a bottom end thereof.
Figure 8:
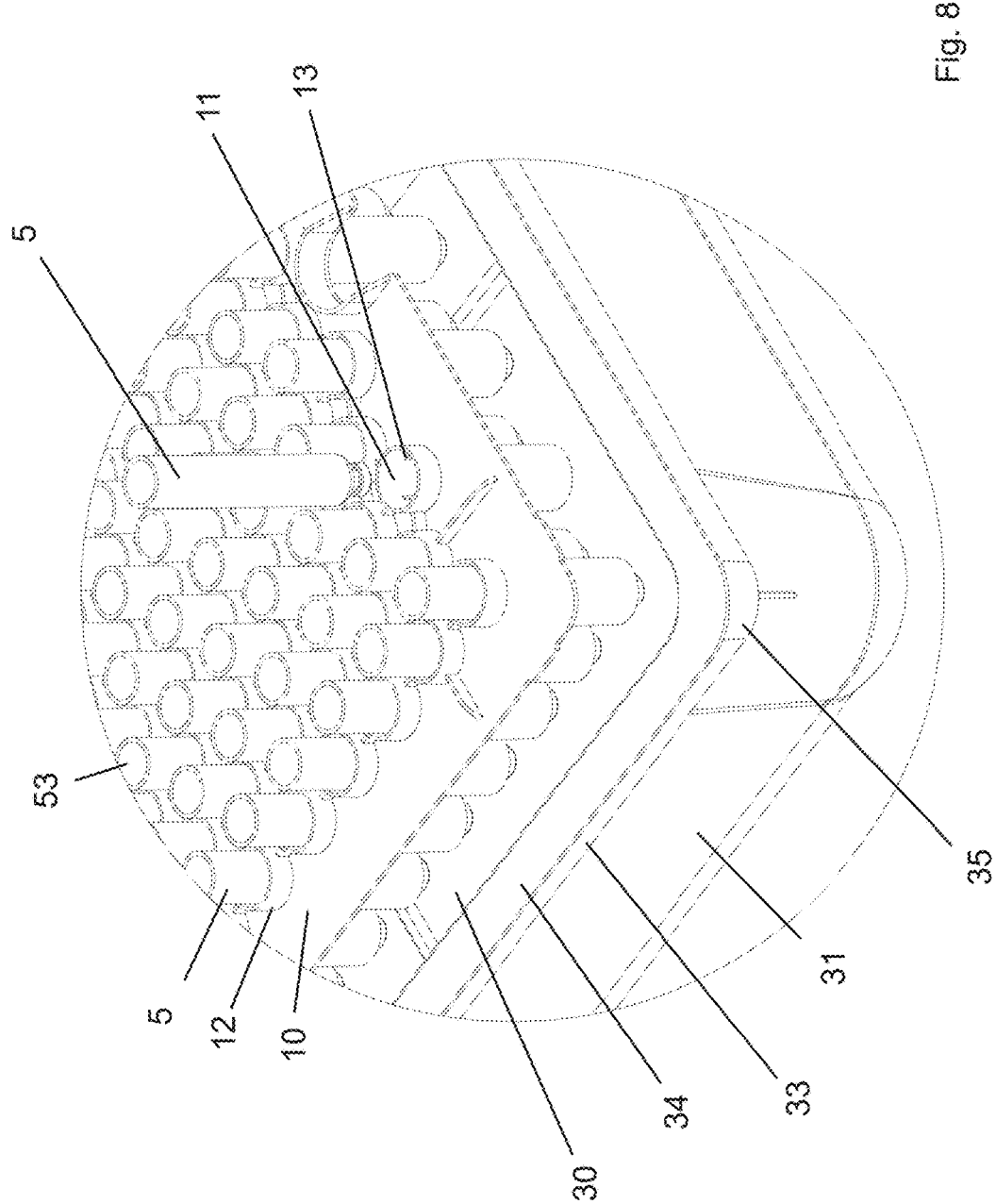
FIG. 8 is an enlarged partial view of the tub and nest assembly of FIG. 7.

For the transport, storage and packaging of a nest 1 as outlined above together with the cartridges accommodated therein a transport or packaging container 3 (hereinafter also named tub) is used as schematically shown in FIG. 7. According to FIG. 7, the transport or packaging container 3 is essentially box-shaped or tub-shaped and has a base 30, a circumferential side wall 31 protruding essentially in vertical direction therefrom, a supporting step 32 protruding essentially rectangular therefrom, a circumferential upper side wall 33 and an upper rim 34 which is formed as a flange. The corners 35 of the transport or packaging container 3 are suitably formed rounded, particularly near the supporting step 32. Preferably, the upper side wall 33 is formed inclined at a small angle of inclination with respect to a vertical to the base 30 in order to ease the insertion of the nest 1. Such a transport or packaging container 3 is preferably formed from a plastics material, particularly by plastic injection molding, and is preferably formed of a clear transparent plastic in order to enable a visual inspection of the nest 1 accommodated in the transport or packaging container 3 and of the cartridges 5 supported by it.

Figure 9:
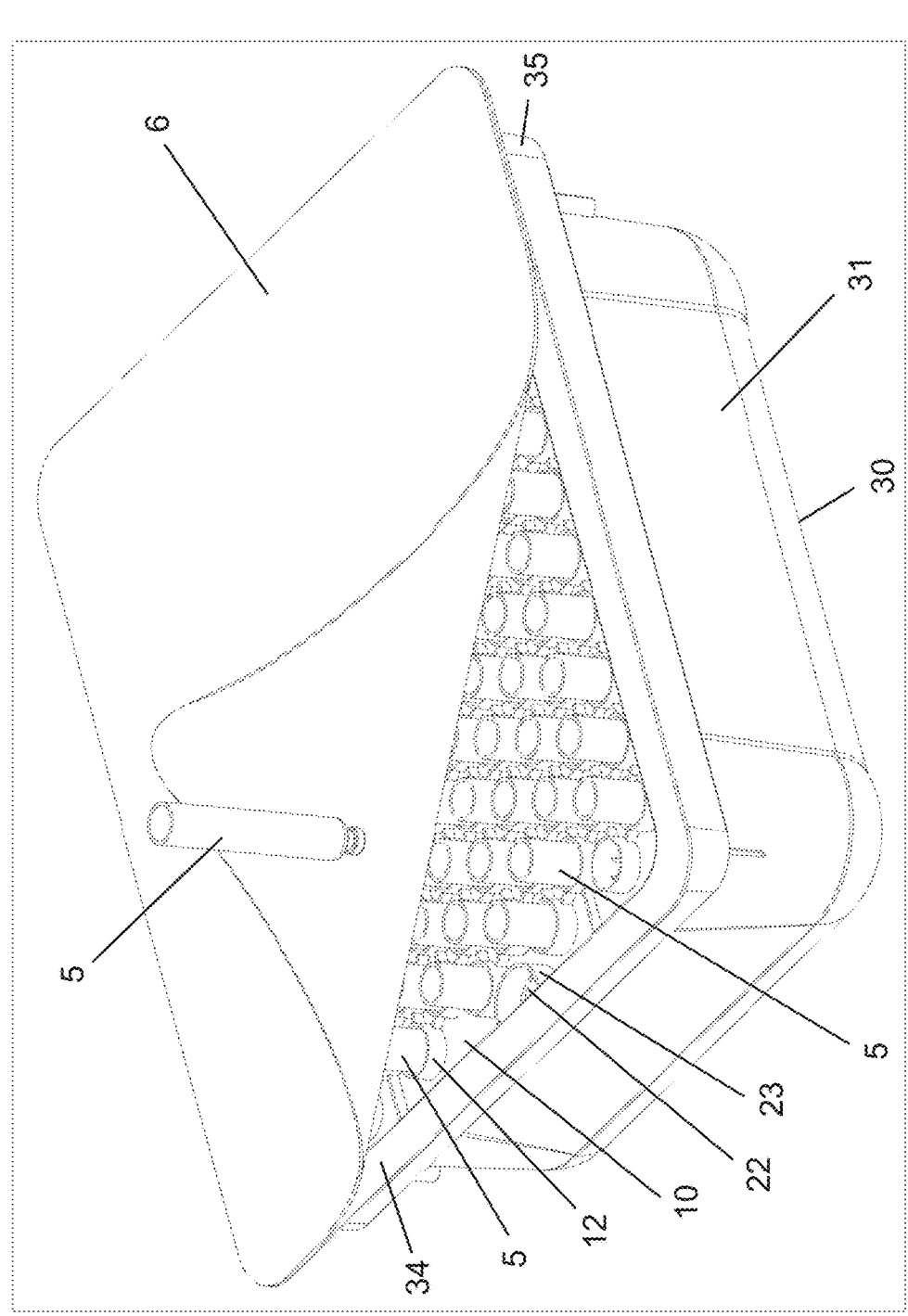
FIG. 9 shows the tub and nest assembly of FIG. 7 with the supporting structure inserted and a sealing lid sealed on an upper edge of the transport or packaging container.

In this manner, the nest 1 can be positioned precisely in the transport or packaging container 3 and thus the plurality of cartridges 5 can be positioned and held in a regular array and at precisely defined positions in a transport or packaging container 3 with standardized dimensions. In particular, it can be ensured in this way that all bottoms or bottom ends of the cartridges are positioned in a plane defined jointly and in parallel to the base 30 and that all upper ends are positioned in a plane defined jointly and parallel to the upper rim 34 of the transport or packaging container 3. As shown in FIG. 9, the upper ends of the cartridges do not extend beyond the upper rim 34 of the transport or packaging container 3 but are spaced apart to the upper rim 34.

As shown in FIG. 9 a packaging unit (also named tub and nest assembly) formed by the transport or packaging container (tub) 3 and the nest 1 with the cartridges 5 accommodated therein is closed or sealed at least on the upper side by means of a protective foil or packaging foil 6 bonded onto the upper flange-like edge 34 of the tub 3. Thus, it is ensured that the interior of tub 3 is hermetically sealed from the environment, from manufacture until the time when access is to be gained to the interior of the tub 3 for further processing of the cartridges 5. The protective foil 6 may be in particular a gas-permeable plastic film, in particular a web of synthetic fibers such as polypropylene fibers (PP) or a Tyvek® protective film, which enables a sterilization of the cartridges accommodated therein through the film 6.

As will become apparent to a person skilled in the art, the bottom side of the transport or packaging container (tub) 3 may also be formed open, e.g. in the manner of the tub 3 shown in FIG. 9, i.e. in the manner that also the bottom side of the tub is provided with a flange-like bottom rim in the manner of the upper rim 34 so that the bottoms of the cartridges 5 may be freely accessible for processing steps also from the underside of the tub 3 if required.

As shown in FIGS. 1 and 2, for enabling an easy insertion of nest 1 into tub 3 and removal from the latter, access apertures 22 are formed on two longitudinal sides of the supporting plate 10, via which gripping arms or the like may grab nest 22. As shown in FIG. 1, the access apertures 22 are partially surrounded by upright side-walls 23 to prevent a collision of the gripping arms or the like with the cartridges accommodated. As shown in FIG. 1, the access apertures 22 are displaced relative to each other, e.g. by one row, which further facilitates an unambiguous positioning of nest 1 in tub 3.

A packaging unit as shown in FIG. 9 accommodating presterilized prefillable cartridges or syringe barrels can be stored under save and sterile conditions and then supplied to pharmaceutical customers for further processing. Particularly, the pharmaceutical customers will then fill medicine or other liquids into the presterilized nested syringe barrels via the filling openings using conventional filling and stoppering machines, which may be any of the three following types of filling and stoppering machines: 1) manual machines, 2) semi automatic machines and 3) fully automatic machines.

An example of such a filling operation is shown in FIG. 11 in a schematic cross-sectional view. At the time of delivery under sterile conditions, the packaging unit will be sealed by a lid or protective foil as outlined above (not shown), while the nest 1 will be supported on the supporting step 32 of tub 3. The cartridges 5, which are sealed by seals 55, e.g. pre-crimped, at their bottom ends will be accommodated upside-down in the receptacles of nest 1 so that their filling openings 53 face toward the upper end of tub 3 and the lid or protective foil (not shown). The height level of the upper ends of cartridges 5 is thus precisely defined in relation to the level of the supporting plate 10, which is essentially equal to the level of supporting step 32 of tub 3, because the supporting plate 10 rests directly on supporting step 32.

The exemplary filling process shown in FIG. 11 considers that the supporting plate 10 rests directly on a rectangular holding frame 40 after removal from tub 3. The inner free width of the holding frame 40, however, also allows for a direct support of the outer side of supporting step 32 on the holding frame. In either case the height level of the upper ends of cartridges 5 is precisely defined in relation to the level of the holding frame 40.

For performing the filling process, the holding frame 40 is transferred at a precisely defined height level to a filling station comprising a row of filling nozzles 41 supported by a holding arm 42 used for injecting a liquid, e.g. a medicine, via the filling openings 53 into the cartridges 5 supported by nest 1. Also the height level of the bottom ends of filling nozzles 41 is precisely defined so that a non-zero gap of well defined width $\Delta z$ will be ensured between the upper ends of the cartridges 5 and the bottom ends of filling nozzles 41. Usually, the width $\Delta z$ of this gap will be precisely adjusted before performing the process and will be part of the general settings of a processing station. The width $\Delta z$ of this gap will be adjusted in accordance with general safety regulations, in particular in accordance with GMP (Good Manufacturing Practice) guidelines requirements.

For a given length of the cartridges 5 to be supported in a nest 1, the height level of the upper ends of the cartridges 5 will be precisely defined by the axial lengths of the receptacles 11 of nest 1 and thus by the height level of the retaining protrusions 15. Thus, if different types of cartridges 5 with different axial lengths are to be processed by one and the same processing station, according to the present invention no change of the general settings of the processing station is required. Rather, only a different type of nest 1 with receptacles 11 of different axial length needs to be used to thereby ensure that also the different type of cartridge 5 will be fed to the processing station at the same height level of the upper ends of the different type cartridges 5.

As the different type of nest 1 required for the different type of cartridge 5 together with the sealed cartridges 5 accommodated therein can be inserted into the packaging unit in the same manner and as the whole packaging unit can be sealed and transported under sterile conditions to the pharmaceutical customers, according to the present invention it can be ensured that also the different type of cartridge may be processed under the same settings and conditions without the need of adjusting the general settings of the processing station. Furthermore, no additional hygienic permissions will be required for this purpose. Thus, according to the present invention different types of cartridges involving different axial lengths may be processed in the same way and under the same general conditions and settings. Thus, the present invention enables a cost-efficient processing of presterilized, sealed cartridges.

As will become apparent to the person skilled in the art, the above principle of replacement of one type of nest by a different type for compensating for different axial lengths of batches of different types of cartridges also works for compensating for different outer diameters of batches of different types of cartridges. More specifically, if a first batch of cartridges having a first outer diameter and a second batch of cartridges having a second outer diameter different to the first outer diameter needs to be processed by the same processing station, according to the invention only a first type of nest used for the first batch of cartridges and having receptacles of a diameter corresponding to the first outer diameter needs to be replaced by a second type of nest to be used for the second batch of cartridges and having receptacles of a diameter corresponding to the second outer diameter.

As will become apparent to the person skilled in the art upon studying of the above, the aforementioned principle may also be applied if access to the bottom ends of the cartridges is required, because also the height level of the bottom ends of all cartridges accommodated by a nest is precisely defined in relation to the height level of the holding frame 40. This even applies if the tub 3 should be supplied to the pharmaceutical customer with an open bottom sealed by a lid or protective foil.

Figure 10:
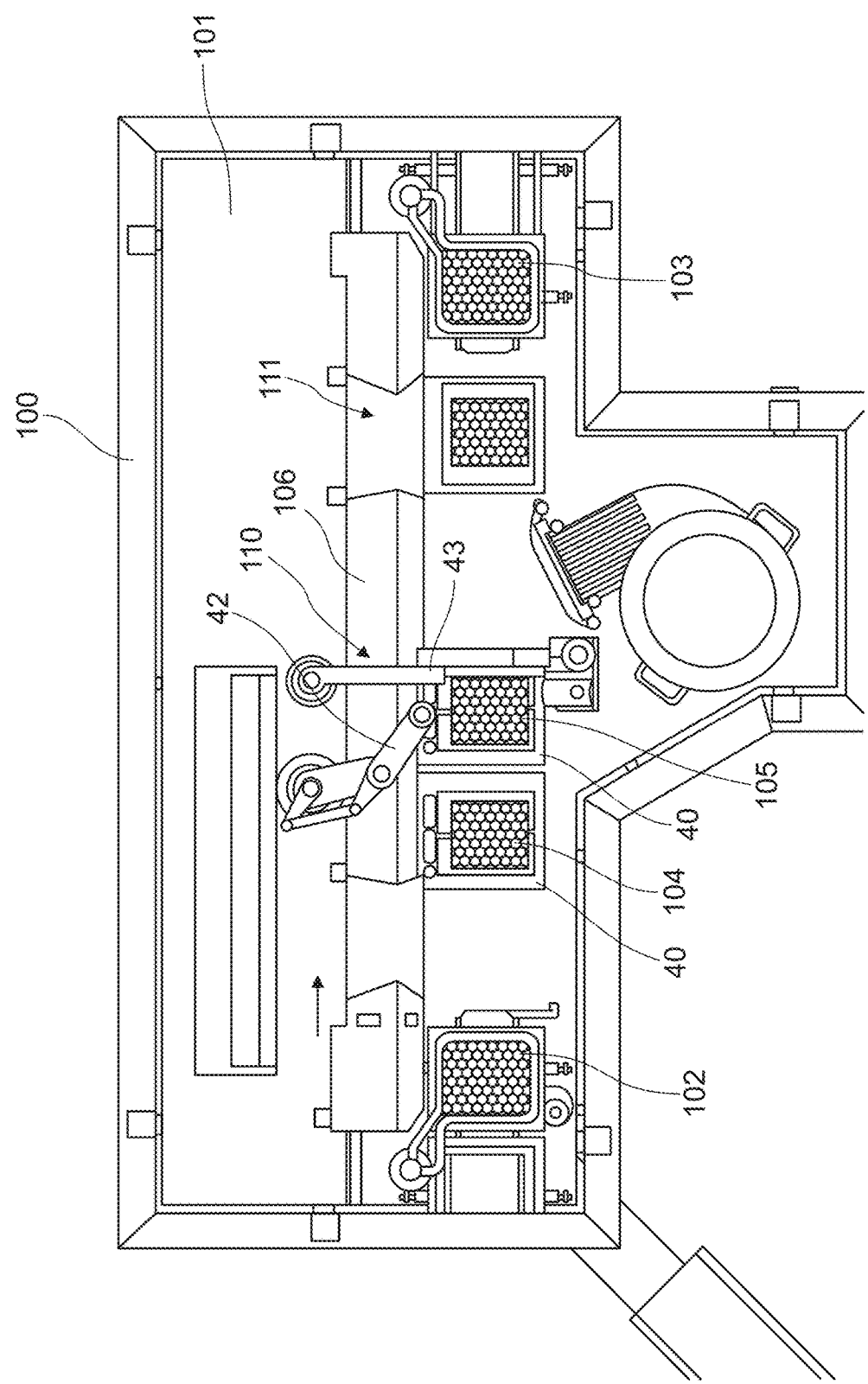
FIG. 10 is a schematic top view of a processing station for processing sealed cartridges using the supporting structure in a process according to the present invention.

FIG. 10 shows in a schematic top view an example of a processing apparatus or station for performing a process according to the present invention, as outlined above, under sterile conditions. The processing apparatus 100 has a sterile inner volume 101 with an infeed section at the left-hand side and an outfeed section at the right-hand side thereof. For processing, sterile packaging units as outlined above are fed, via the infeed section, into the sterile inner volume 101. During this infeed step the lids or protective foils of the packaging units are removed so that the tub and nest assemblies accommodating the presterilized cartridges finally are disposed near the infeed position indicated by reference numeral 102. For processing, the tub and nest assemblies are conveyed by a conveyer 106 along the direction of the arrow shown in FIG. 10 until finally reaching the outfeed position indicated by reference numeral 103. For conveying the nests either the nests are accommodated by holdings frames 40 or similar holding tables or the tubs respectively accommodating a nest are accommodated by holdings frames 40 or similar holding tables. In any case, the upper ends of the cartridges are fed to the processing stations 101 at precisely defined height levels.

As an example for a process step, FIG. 10 shows the filling and stoppering of the cartridges accommodated by nests in the holding frames 40. For the filling and stoppering, the nests or tub and nest assemblies are first conveyed to the waiting position 104 and then to the filling and stoppering station 110, where the filling and stoppering process is usually performed row-wise. After filling and stoppering the nests or tub and nest assemblies are finally conveyed to the outfeed position indicated by reference numeral 103.

During stoppering of the cartridges, when usually large axial forces will be exerted from above onto the cartridges, the symmetric arrangement of the retaining protrusions 15 (see FIG. 2) together with that of the axial ribs 13 ensures a symmetric distribution of such forces with only minor deformation of the general shape of the receptacles 11 and of the retaining protrusions 15 so that both the precise centering and the height levels of the cartridges will be maintained.

Besides filling the sealed cartridges via the filling openings at the upper ends and/or stoppering the sealed cartridges at their upper ends using rubber stoppers, the above procedure may equally be performed for pre gassing or post gassing the cartridges. As can be concluded from FIGS. 2 and 4, the gaps formed between the axial ribs 13 of the receptacles together with the gaps 16 between the retaining protrusions 15 of the receptacles and the access apertures 22 further support a proper gas flow for pre gassing or post gassing of the cartridges when the nest is accommodated in a tub, because a sterilizing gas may flow essentially unhindered from the upper side of the nest towards the bottom side of the nest, if accommodated in a tub.

It will be appreciated that according to the present invention the sealed, particularly pre-crimped, cartridge barrels are entirely of a known form and require no modification as compared to a conventional sealed cartridge barrels. Equally the tub is as currently employed in a known prefillable syringe handling system and it is only the nest which has been modified in such a way that it will be interchangeable to a conventional nest of prefillable syringe nest in terms of height level of sealed cartridge barrels in tub as well as on the filling machine table or holding frame. Moreover, as the sealed cartridges allows to use the same height setting of a prefillable syringe filling machine table, the down stand socket of the receptacles ensure that the sealed cartridge barrels are held at the same level of prefillable syringes in a conventional nest.

Thus, the supporting structure according to the present invention may be used equally for a manual, semiautomatic or fully-automatic filling and stoppering process, as summarized below:

1) Manual Filling and Stoppering Machine for Prefillable Syringes

Normally this manual filling and stoppering machine as the name suggests is used for filling and stoppering of prefillable syringes in a non-automated process. According to the present invention the customer can fill the medicine into other types of medical devices, i.e. into cartridges having a different axial length, while using the same filling and stoppering machine because the nest and tub assembly according to the present invention enables performing the same processing steps on same machine without any change in filling machine parts and any change in machine setting.

Thus, keeping different change parts and different settings and also the requirement of separate validation studies can be avoided, which otherwise will add on to the costs and also will require additional time to change the parts resulting in production loss.

In case of a stoppering machine only the fixture top plate needs to be changed to match the nest design if required without changing the height of the fixture.

2) Semi-Automatic Filling and Stoppering Machine for Prefillable Syringes

Normally this semi-automatic filling and stoppering machine as the name suggests is also used for filling and stoppering of prefillable syringes. According to the present invention the customer can fill the medicine into other types of medical devices, i.e. into cartridges having a different axial length, while using the same filling and stoppering machine because the nest and tub assembly according to the present invention enables performing the same processing steps on same machine without any change in filling machine parts and any change in machine setting, particularly without any change in the filling table height. The same advantages result as outlined above for manual Filling and stoppering machines.

3) Fully-Automatic Filling and Stoppering Machine for Prefillable Syringes

The nested tub for sealed, particularly pre-crimped, pre-sterilized cartridges according to the present invention can be directly fed on existing fully-automatic filling and stoppering machines of prefillable syringes without any setting change in the machine and without adjustment or change in the filling table height and only by replacement of one change part i.e. carrier resting plate to match the nest design if required.

The following further advantages of the inventive nest for cartridges exist:

1) The nest design is developed in such a way that the top level of the cartridges in the tub and nest is maintained exactly at the same top height as that of prefillable syringe in conventional tub and nest format.

2) Ribs are provided on the top and/or bottom surface of the nest for maintaining the surface of the nest in horizontal position without bending or cave in downwards towards the tub.

3) The retaining protrusions of each socket have a flower type profile (shown in FIGS. 3 and 4) to hold the sealed cartridges at the shoulder portions. The bottom flower type profile is designed in such a way that it can hold the cartridge stably throughout it's processing, especially during stoppering operation where maximum forces are applied on the nest bottom flower type profile. Bottom flower type profile can sustain up to 1,000 N force.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

LIST OF REFERENCE NUMERALS

1 supporting structure (also named nest)
3 transport or packaging container (also named tub)
4 tub and nest assembly
5 cartridge
6 sealing lid
10 (planar) holding plate
11 receptacle
12 side wall of receptacle 11 on upper side
13 axial rib
14 side wall of receptacle 11 on bottom side
15 retaining protrusion
16 gap between retaining protrusions 15
17 central opening
20 rounded corner
21 extension
22 gripping aperture
23 side wall of gripping aperture 22
24 guiding web
25 guiding web
26 stiffening web on upper side
27 stiffening web on bottom side
28 stiffening web on bottom side
30 bottom
31 lower side wall
32 supporting step
33 upper side wall
34 upper flange
35 rounded corner
40 holding frame
41 filling nozzle
42 holding arm for filling array of nozzles 41
43 holding arm for stoppering devices
50 cylindrical body
51 shoulder portion
52 widened upper rim
53 filling opening
54 bottom opening
55 seal
100 processing apparatus
101 sterile inner volume
102 tub and nest assembly at infeed
103 tub and nest assembly at outfeed
104 nest assembly at waiting position
105 nest assembly at filling station
106 conveyor
110 process station for filling and stoppering
111 downstream processing station

The invention claimed is:

1. A supporting structure for supporting a plurality of pre-crimped cartridges for use in pharmaceutical, medical or cosmetic applications, said pre-crimped cartridges having
an upper end and a bottom end opposite to the upper end,
a cylindrical body of a first outer diameter with a filling opening at the upper end, and
a shoulder portion at the bottom end, which is followed by a widened bottom rim with a secondary opening for drug administering, wherein the secondary opening is sealed by a seal and an outer closure is crimped over the widened bottom rim to secure the seal at the cartridge, a predetermined axial length being defined between the upper end and the bottom end, wherein an outer diameter of the pre-crimped cartridges at their shoulder portions is larger than the outer diameter at their sealed bottom ends but smaller than the first outer diameter,
said supporting structure comprising:
a planar supporting plate, and
a plurality of tubular receptacles formed at the planar supporting plate in a regular arrangement and formed by circumferential side-walls extending downward from a bottom side of the planar supporting plate for accommodating the pre-crimped cartridges, wherein
retaining protrusions are formed at the bottom ends of the receptacles protruding inward, and
the axial length of the receptacles is smaller than the axial length of the pre-crimped cartridges,
characterized in that
the retaining protrusions are mated with the shoulder portions of the pre-crimped cartridges in such a manner that the shoulder portions of the pre-crimped cartridges are supported on the retaining protrusions of the receptacles, that the sealed bottom ends of the pre-crimped cartridges extend through openings formed by the retaining protrusions at the bottom ends of the receptacles and that the upper ends of the pre-crimped cartridges protrude from the upper ends of the receptacles at an upper side of the planar supporting plate, when the pre-crimped cartridges are accommodated upside-down in the receptacles, wherein for stiffening the supporting plate
stiffening ribs provided on the bottom side of the supporting plate interconnect outer ones of the receptacles, and/or
stiffening ribs provided on the bottom side and near the center of the supporting plate interconnect central ones of the receptacles.

2. The supporting structure as claimed in claim 1, wherein the receptacles are of cylindrical shape and
a plurality of ribs are formed at equidistant angular spacing on inner circumferential side-walls of the receptacles,
said ribs protruding radially inward from the inner circumferential side-walls of the receptacles for centering the pre-crimped cartridges inside the receptacles.

3. The supporting structure as claimed in claim 1, wherein the retaining protrusions are formed as ring segments that protrude radially inward at the bottom ends of the receptacles and at equidistant angular spacing.

4. The supporting structure as claimed in claim 3, wherein
the thickness of the retaining protrusions in the axial direction is smaller than the axial length of the sealed bottom ends,
so that the sealed bottom ends of the pre-crimped cartridges extend through openings formed by the retaining protrusions at the bottom ends of the receptacles.

5. The supporting structure as claimed in claim 1, wherein
the supporting plate is formed of a plastic material and
the side-walls of the receptacles and the retaining protrusions are formed unitary with the supporting plate, wherein
the retaining protrusions are configured to sustain axial forces exerted onto the pre-crimped cartridges of up to 1,000 N.

6. The supporting structure as claimed in claim 1, wherein the front ends of the retaining protrusions are wedge-shaped in correspondence with an outer contour of the shoulder portions of the pre-crimped cartridges.

7. The supporting structure as claimed in claim 2, wherein
virtual connecting lines between the centers of directly adjacent receptacles respectively form a hexagon with a further receptacle disposed at a center of the respective hexagon,
the receptacles extend beyond the upper surface of the supporting plate and
stiffening ribs protruding upward from the upper surface of the supporting plate are formed on the upper surface of the supporting plate so as to connect the circumferential side walls of the receptacles, for stiffening the supporting plate.

8. A transport or packaging container for accommodating a plurality of pre-crimped cartridges for use in pharmaceutical, medical or cosmetic applications, wherein
the transport or packaging container is box-shaped and comprises:
a bottom, which is closed or sealed by a seal,
upstanding lower side-walls extending essentially perpendicularly from said bottom,
a circumferential supporting step extending horizontally from said side-walls,
upper side-walls extending upward from said supporting step,
a circumferential flange formed at upper ends of the upper side-walls, and
a supporting structure as claimed in claim 1 disposed inside the transport or packaging container and accommodating a plurality of pre-crimped cartridges in the receptacles thereof in such a manner, that the shoulder portions of the pre-crimped cartridges are supported on the retaining protrusions of the receptacles, that the sealed bottom ends of the pre-crimped cartridges extend through openings formed by the retaining protrusions at the bottom ends of the receptacles and that the upper ends of the pre-crimped cartridges protrude from the upper ends of the receptacles at an upper side of the planar supporting plate,
wherein
the edge of the planar supporting plate of the supporting structure is supported on the circumferential supporting step,
the upper ends of the pre-crimped cartridges are disposed at the same height level but do not protrude beyond the circumferential flange of the transport or packaging container, and
the bottom ends of the pre-crimped cartridges are disposed spaced apart from the bottom of the transport or packaging container.

9. The transport or packaging container as claimed in claim 8, further comprising a flexible lid sealed onto the circumferential flange of the transport or packaging container for sealing the transport or packaging container.

10. A process for processing a batch of pre-crimped cartridges for use in pharmaceutical, medical or cosmetic applications,
said cartridges having
an upper end and a bottom end opposite to the upper end,
a cylindrical body of a first outer diameter with a filling opening at the upper end, and
a shoulder portion at the bottom end, which is followed by a widened bottom rim with a secondary opening for drug administering, wherein the secondary opening is sealed by a seal and an outer closure is crimped over the widened bottom rim to secure the seal at the cartridge,
a predetermined axial length being defined between the upper end and the bottom end, wherein an outer diameter of the pre-crimped cartridges at their shoulder portions is larger than the outer diameter at their sealed bottom ends but smaller than the first outer diameter;
said process comprising the steps of:
a) providing a supporting structure comprising
a planar supporting plate, and
a plurality of tubular receptacles formed at the planar supporting plate in a regular arrangement and formed by circumferential side-walls extending downward from a bottom side of the planar supporting plate for accommodating the pre-crimped cartridges, wherein retaining protrusions are formed at the bottom ends of the receptacles protruding inward, and
the axial length of the receptacles is smaller than the axial length of the pre-crimped cartridges;
b) disposing the pre-crimped cartridges upside-down in the receptacles and with their upper ends protruding from the upper ends of the receptacles at an upper side of the planar supporting plate so that the shoulder portions of the pre-crimped cartridges are supported on the retaining protrusions of the receptacles, that the sealed bottom ends of the pre-crimped cartridges extend through openings formed by the retaining protrusions at the bottom ends of the receptacles and that the upper ends of the pre-crimped cartridges are disposed at the same height level;
c) feeding the supporting structure with the pre-crimped cartridges to a processing station; and
d) processing the pre-crimped cartridges at their upper ends at the processing station while being supported by the supporting structure;
wherein step d) comprises at least a step of stoppering the pre-crimped cartridges at their upper ends using rubber stoppers.

11. The process as claimed in claim 10, wherein step d) comprises one or more of the following:
filling the pre-crimped cartridges via the filling openings at the upper ends; pre gassing and post gassing.

12. The process as claimed in claim 10, further comprising
disposing the supporting structure in a frame-like holding table;
feeding the supporting structure together with the pre-crimped cartridges to the processing station while being supported by the frame-like holding table; and
disposing the supporting structure with the pre-crimped cartridges inside a box-shaped transport or packaging container after said step d), which comprises a bottom, upstanding lower side-walls extending essentially perpendicularly from said bottom, a circumferential supporting step extending horizontally from said side-walls, upper side-walls extending upward from said supporting step and a circumferential flange formed at upper ends of the side-walls so that
the edge of the planar supporting plate of the supporting structure is supported on the circumferential supporting step of the transport or packaging container,
the upper ends of the pre-crimped cartridges do not protrude beyond the circumferential flange of the transport or packaging container, and
the bottom ends of the pre-crimped cartridges are disposed spaced apart from the bottom of the transport or packaging container.

13. The process as claimed in claim 10, further comprising:
disposing the supporting structure with the pre-crimped cartridges inside a box-shaped transport or packaging container, which comprises a bottom, upstanding lower side-walls extending essentially perpendicularly from said bottom, a circumferential supporting step extending horizontally from said side-walls, upper side-walls extending upward from said supporting step and a circumferential flange formed at upper ends of the upper side-walls so that
the edge of the planar supporting plate of the supporting structure is supported on the circumferential supporting step,
the upper ends of the pre-crimped cartridges do not protrude beyond the circumferential flange of the transport or packaging container, and
the bottom ends of the pre-crimped cartridges are disposed spaced apart from the bottom of the transport or packaging container; wherein
step c) further comprises:
disposing the transport or packaging container in a frame-like holding table so that the supporting step of the transport or packaging container is supported on an upper side of the frame-like holding table and that the upper ends of the pre-crimped cartridges are disposed at the same height level; and
feeding the frame-like holding table together with the transport or packaging container, the supporting structure accommodated therein and the pre-crimped cartridges to the processing station.

14. The process as claimed in claim 12, further comprising sealing the transport or packaging container with a flexible lid.

15. A combination of a supporting structure and a plurality of pre-crimped cartridges for use in pharmaceutical, medical or cosmetic applications supported by said supporting structure, said pre-crimped cartridges having
an upper end and a bottom end opposite to the upper end,
a cylindrical body of a first outer diameter with a filling opening at the upper end, and
a shoulder portion at the bottom end, which is followed by a widened bottom rim with a secondary opening for drug administering, wherein the secondary opening is sealed by a seal and an outer closure is crimped over the widened bottom rim to secure the seal at the cartridge,
a predetermined axial length being defined between the upper end and the bottom end, wherein an outer diameter of the pre-crimped cartridges at their shoulder portions is larger than the outer diameter at their sealed bottom ends but smaller than the first outer diameter,
said supporting structure comprising:
a planar supporting plate, and
a plurality of tubular receptacles formed at the planar supporting plate in a regular arrangement and formed by circumferential side-walls extending downward from a bottom side of the planar supporting plate for accommodating the pre-crimped cartridges, wherein retaining protrusions are formed at the bottom ends of the receptacles protruding inward, and the axial length of the receptacles is smaller than the axial length of the pre-crimped cartridges, wherein the pre-crimped cartridges are accommodated upside-down in the receptacles of the supporting structure, characterized in that the shoulder portions of the pre-crimped cartridges are supported on the retaining protrusions of the receptacles, that the sealed bottom ends of the pre-crimped cartridges extend through openings formed by the retaining protrusions at the bottom ends of the receptacles and that the upper ends of the pre-crimped cartridges protrude from the upper ends of the receptacles at an upper side of the planar supporting plate, wherein for stiffening the supporting plate stiffening ribs provided on the bottom side of the supporting plate interconnect outer ones of the receptacles, and/or stiffening ribs provided on the bottom side and near the center of the supporting plate interconnect central ones of the receptacles.

16. The combination of a supporting structure and a plurality of pre-crimped cartridges as claimed in claim 15, wherein the receptacles are of cylindrical shape and a plurality of ribs are formed at equidistant angular spacing on inner circumferential side-walls of the receptacles, said ribs protruding radially inward from the inner circumferential side-walls of the receptacles, wherein the pre-crimped cartridges are centered inside the receptacles by the ribs.

17. The combination of a supporting structure and a plurality of pre-crimped cartridges as claimed in claim 15, wherein the retaining protrusions are formed as ring segments that protrude radially inward at the bottom ends of the receptacles and at equidistant angular spacing.

18. The combination of a supporting structure and a plurality of pre-crimped cartridges as claimed in claim 17, wherein the thickness of the retaining protrusions in the axial direction is smaller than the axial length of the sealed bottom ends.

19. The combination of a supporting structure and a plurality of pre-crimped cartridges as claimed in claim 15, wherein the supporting plate is formed of a plastic material and the side-walls of the receptacles and the retaining protrusions are formed unitary with the supporting plate, wherein the retaining protrusions are configured to sustain axial forces exerted onto the pre-crimped cartridges of up to 1,000 N.

* * * * *